(12) United States Patent
Ramey

(10) Patent No.: US 6,854,620 B2
(45) Date of Patent: Feb. 15, 2005

(54) DRIVE SYSTEM FOR AN INFUSION PUMP

(75) Inventor: Kirk Ramey, Bedford, VA (US)

(73) Assignee: Nipro Diabetes, Systems, Inc., Miramar, FL (US)

(*) Notice: Subject to any disclaimer, the term of this patent is extended or adjusted under 35 U.S.C. 154(b) by 66 days.

(21) Appl. No.: 10/121,318

(22) Filed: Apr. 12, 2002

(65) Prior Publication Data

US 2003/0009133 A1 Jan. 9, 2003

Related U.S. Application Data

(60) Provisional application No. 60/283,815, filed on Apr. 13, 2001.

(51) Int. Cl.[7] .............................. B67D 5/08; B67D 5/42
(52) U.S. Cl. .................... 222/63; 222/153.13; 222/327; 222/333; 222/390; 604/154
(58) Field of Search .............................. 222/63, 153.13, 222/325–327, 333, 386, 390; 604/152–155

(56) References Cited

U.S. PATENT DOCUMENTS

| | | | | |
|---|---|---|---|---|
| 3,623,474 A | * | 11/1971 | Heilman et al. ............ 600/432 |
| 4,583,974 A | * | 4/1986 | Kokernak .................... 604/211 |
| 4,952,205 A | * | 8/1990 | Mauerer et al. ............... 604/67 |
| 5,993,423 A | * | 11/1999 | Choi ........................... 604/155 |
| 6,659,980 B2 | * | 12/2003 | Moberg et al. ............. 604/154 |

* cited by examiner

*Primary Examiner*—Gene Mancene
*Assistant Examiner*—Patrick Buechner
(74) *Attorney, Agent, or Firm*—Christopher & Weisberg, P.A.

(57) ABSTRACT

A pump system for an infusion system includes a linear drive (36, 36') which minimizes the space occupied by the pump components in a portable housing (10, 10'). A motor (34) and a motor drive shaft (42) are arranged in parallel with, and adjacent to a syringe (14, 14') and lead screw (94, 94'). A gear box (54) connects the drive shaft and lead screw to transfer rotational movements between them. A piston driving member, such as a cone (116) or drive nut (116') converts the rotational movement of the lead screw into linear motion of a syringe piston (24). Sensors (150, 152) detect when the piston or cone is in a "home" position and in an "end" position, respectively. Optionally, a proximity sensor (170) is used to ensure that the cone and the piston (24) are abutting during dispensing. Alternatively, a clamping member (350) selectively clamps the lead screw (94') against linear motion in at least a dispensing direction.

24 Claims, 10 Drawing Sheets

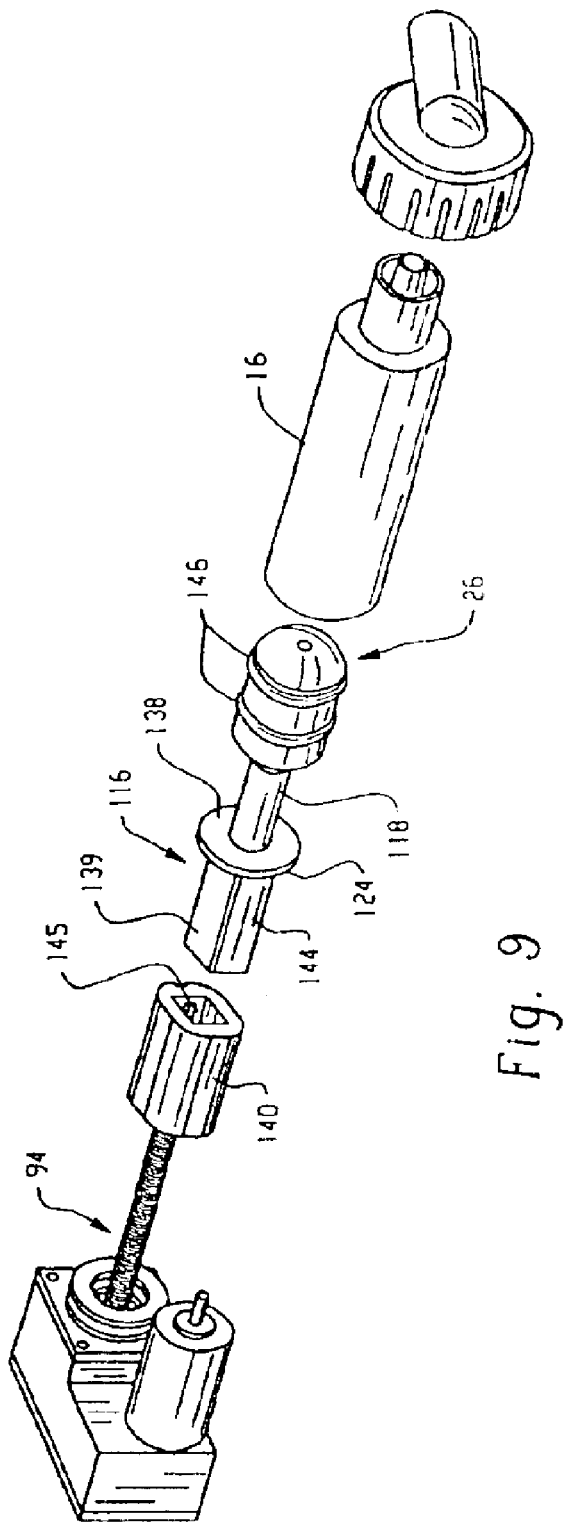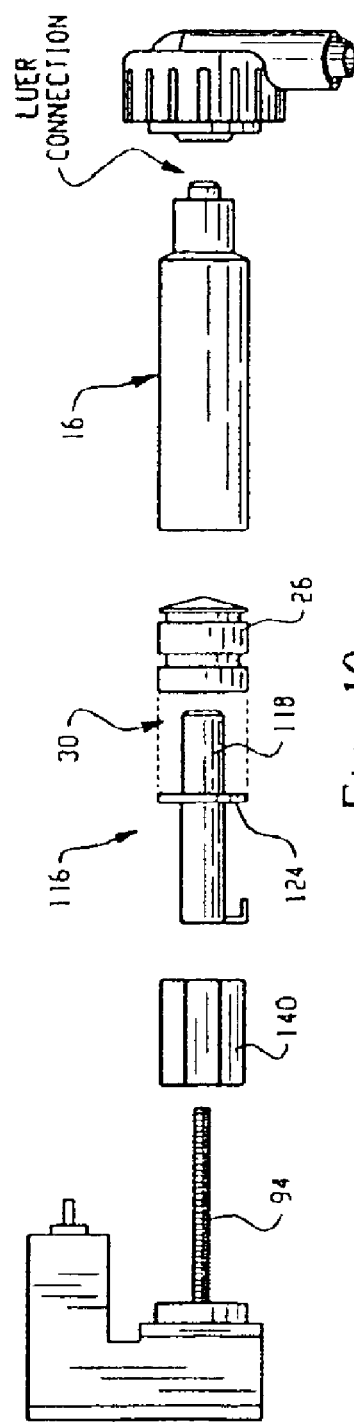
Fig. 9
Fig. 10

DRIVE SYSTEM FOR AN INFUSION PUMP

This application claims the priority of U.S. Provisional Application Ser. No. 60/283,815, filed Apr. 13, 2001.

BACKGROUND OF THE INVENTION

The present invention relates to a portable pump for delivery of a medicament, such as insulin, from a syringe, and will be described with particular reference thereto. It should be appreciated, however, that the invention also has application in the miniaturization of pumps for delivery of other liquid substances.

Insulin pump systems which use a piston-operated cartridge for delivery of a medicament, such as insulin, allow patients to administer safely doses of an intravenous or subcutaneous medication at will, without the need for constant supervision by medical staff. These devices often include a housing, which is small enough to fit in a patient's pocket, that houses the cartridge, a motor, and a drive system. A power supply, such as a battery, is also included for supplying power to the motor. The outside of the housing provides key pad entry for allowing the patient to program the rate of insulin delivery and to modify the delivery rate according to the patient's expected or actual carbohydrate intake. To increase the portability of the infusion pump, a smaller housing is desirable. However, current designs for infusion pumps limit the overall minimum length of the housing.

The present invention provides for a new and improved pump system, which overcomes the above-referenced problems, and others.

SUMMARY OF THE INVENTION

In accordance with one aspect of the present invention, a liquid delivery system is provided. The system includes a housing which accommodates a syringe containing the liquid. A motor is carried by the housing. A drive system, operatively connected with the motor, advances a piston of the syringe to expel liquid from a barrel of the syringe. The drive system includes a threaded rotatable shaft and a piston drive member, which linearly advances the piston, the drive member defining a threaded portion which engage threads of the shaft, the piston drive member advancing linearly as the shaft rotates.

In accordance with another aspect of the present invention, an infusion system is provided. The infusion system includes a housing for supporting a cartridge. The cartridge includes a chamber which holds a medicament and a means for expelling the medicament from the chamber. A means is provided for linearly advancing the means for expelling the medicament. A sensor means detects at least one of an abutting relationship and a lack of an abutting relationship between the advancing means and the expelling means.

In accordance with another aspect of the present invention, an infusion system is provided. The system includes a housing which receives a cartridge, the housing defining an opening for receiving the cartridge therethrough. A threaded shaft is selectively drivingly coupled with a piston of the cartridge, the threaded shaft linearly advancing the piston as the shaft rotates to expel a liquid from a barrel of the cartridge. A clamping member is selectively actuated to engage the shaft and thereby inhibit linear advancement of the shaft, relative to the barrel.

In accordance with another aspect of the present invention, a method of dispensing a liquid from a barrel of a cassette having a piston is provided. The method includes bringing a piston drive member and the piston into an abutting relationship. The piston drive member is advanced to advance the piston to dispense the fluid from the barrel. In the event that a change in ambient pressure causes the piston to separate from the piston drive member, the method includes detecting that the separation has occurred, and alerting a user of the cassette that a condition associated with the separation has occurred.

In accordance with another aspect of the present invention, a method of dispensing a medicament from a cartridge including a barrel and a piston is provided. The method includes bringing a piston drive member and the piston into an abutting relationship in a first position, sensing that the piston drive member is in the first position and sending a signal to a controller. The piston drive member is advanced incrementally under the control of the controller to advance the piston to dispense the fluid from the barrel until the piston drive member is in a second position linearly spaced from the first position. Further, the method includes sensing that the piston drive member is in the second position and sending a signal to a controller.

In accordance with another aspect of the present invention, a method of dispensing a liquid from a barrel of a cassette having a piston is provided. The method includes coupling a piston drive member to the piston, the piston drive member carrying a rotatable shaft. A clamping means is actuated which clamps the shaft against linear motion in a dispensing direction. The clamped shaft is rotated to advance the piston drive member and the piston to dispense the fluid from the barrel.

One advantage of at least one embodiment of the present invention is that it reduces the size of an infusion pump for improved portability.

Another advantage of at least one embodiment of the present invention is that occlusions in an infusion line are detected.

Yet another advantage of at least one embodiment of the present invention is that the end of travel of the drive mechanism is detected.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 9 is an exploded perspective view of the lead screw, guide member, drive member, piston, barrel, and cap of FIG. 1;

FIG. 10 is an exploded side view of the lead screw, guide member, drive member, piston, barrel, and cap of FIG. 1;

DETAILED DESCRIPTION OF THE PREFERRED EMBODIMENTS

Figure 1:
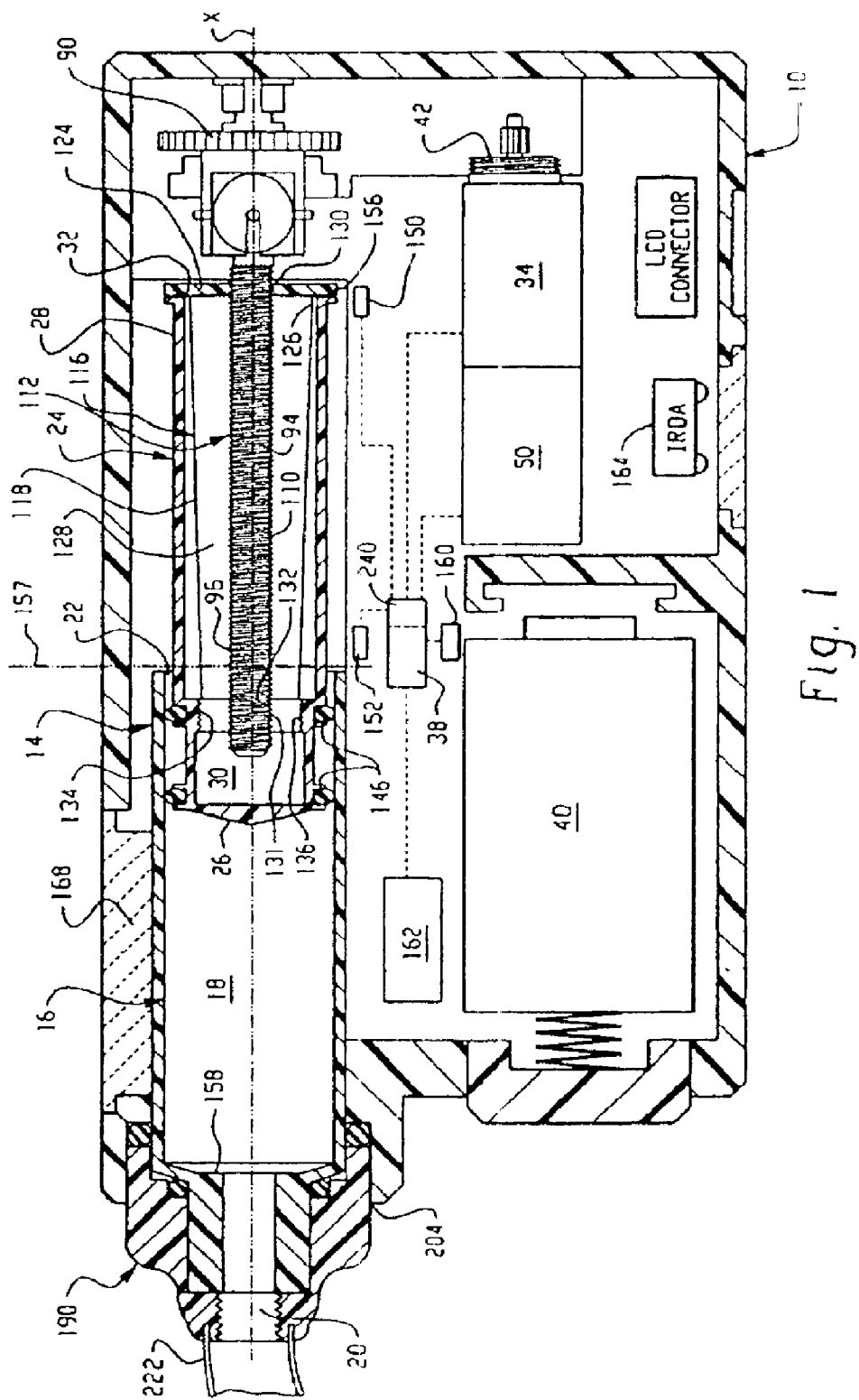
FIG. 1 is a side sectional view of an infusion pump system according to the present invention, with the gear box removed.

With reference to FIG. 1, a portable pump system for use in an ambulatory injection system, such as an insulin injection system, is shown. The system includes a housing 10, which is designed to fit conveniently in the pocket of a user or to be attached to a belt clip. A cassette 14, such as a disposable or reusable syringe, is selectively received within the housing 10. The syringe 14 holds a supply of a medicament, such as insulin, for injection into a diabetic person, or other user in need of the medicament. The syringe 14 includes a barrel 16, which defines an internal chamber 18 for holding the medicament, a dispensing outlet 20 connected with one end of the barrel 16, and an opening 22 at an opposite end of the barrel 16. A plunger or piston 24 is received within the barrel 16 via the opening 22 for reciprocal motion within the barrel 16 for ejecting the medicament from the barrel. The piston 24 includes a head portion or cap 26, which seals the opening 22, and a longitudinally extending cylindrical or frustoconical portion 28, extending from the head portion, which defines an internal piston chamber 30 with an open end 32 furthest from the barrel 16.

Figure 2:
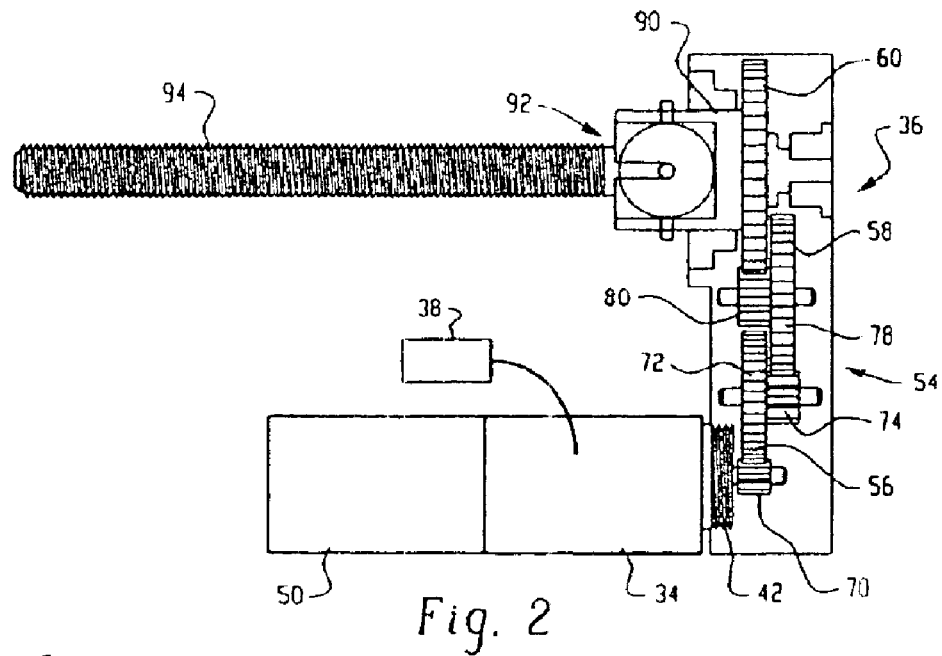
FIG. 2 is a side sectional view of the lead screw, gear box, drive shaft, and motor of the infusion pump system of FIG. 1.

With reference also to FIG. 2, mounted within the housing 10, are a motor 34 and a drive system 36 for incrementally advancing the piston 24 to eject aliquots of the medicament according to a preprogrammed injection schedule. The motor 34 is under the control of a microprocessor-controller 38, which is preferably housed within the housing 10. Power for the motor and other operative components of the pump system is supplied by a battery 40, or other source of power. The motor 34 is preferably a stepper motor, which rotates in finite, small increments or steps. The drive system 36 includes a drive shaft 42, which is coupled to the motor so that it rotates a small portion of a revolution with each step of the motor. For example, the motor 34 may advance twenty steps to turn the drive shaft 42 one complete revolution. As shown in FIG. 1, the drive shaft 42 is aligned generally in parallel with the longitudinal axis x of the syringe barrel 16 and piston 24 and rotates generally perpendicular thereto about an axis parallel with the x axis.

An encoder 50 is attached to an armature of the motor 34 to detect when the steps are occurring. For example, a two-phase encoder alternatively registers a "zero" or a "one" output with each successive step. The microprocessor-controller 38 is equipped with processing software or hardware to detect the change in output of the encoder and thereby determine whether the motor 34 is advancing as instructed. The motor shaft 42 in turn drives a gearbox 54 comprising a series of gears 56, 58, 60, as shown in greater detail in FIG. 2. The number and size of the gears will depend on the desired ratio of drive shaft rotation to output rotation.

Figure 3:
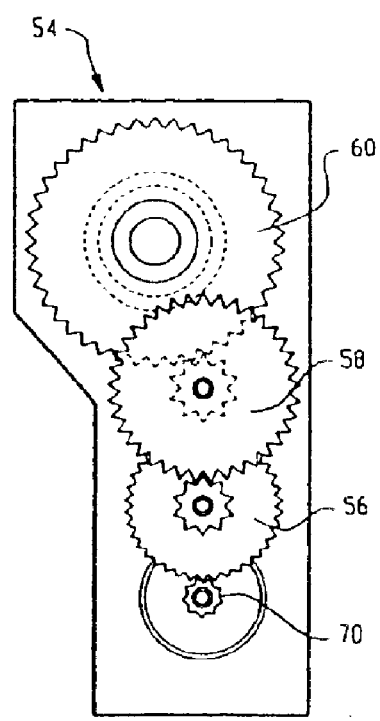
FIG. 3 is a schematic view of the gear box of FIG. 1.

As shown in FIGS. 2 and 3, the gearbox 54, by way of example has three gears 56, 58, and 60. Gears 56, and 58 are cluster gears, which each have a larger spur portion and a smaller pinion portion connected thereto. As shown in FIG. 2, the drive shaft 42 has a toothed-portion 70 at its distal end, having, for example 9 teeth, which drives a spur 72 of the gear 56 (having, for example 38 teeth), thereby turning an associated pinion 74 (having, for example 10 teeth). The pinion 74 in turn engages a spur 78 (having, for example 37 teeth) of the second gear 58, which in turn turns the pinion 80 (having, for example ten teeth) of the second gear. The pinion 80 engages teeth on the third gear 60, which forms a part of a universal yoke element 90.

Figure 4:
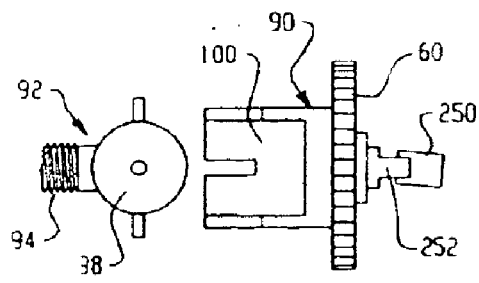
FIG. 4 is an enlarged view of the yoke and lead screw of FIG. 1.
Figure 5:
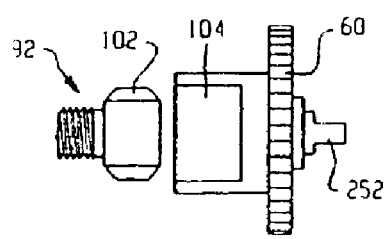
FIG. 5 is an alternative view of the yoke and lead screw of FIG. 1.

As shown in FIG. 4, the yoke element 90 is selectively connectable with a first portion, or driven end 92 of a threaded, rotatable shaft or lead screw 94. Thus, the rotations of the motor shaft 42 are transferred to the lead screw via the gear box 54 at a selected ratio, for example a ratio of about 60:1 (60 rotations of the motor shaft for each rotation of the lead screw). A second, or distal end 96 (FIG. 1) of the lead screw 94 drives the piston 24 towards the chamber, so that the medicament is expelled. Specifically, the lead screw 94 is received longitudinally within the piston chamber 30 and extends generally parallel to the drive shaft 42. As shown in FIG. 4, the driven end 92 may comprise a ball and pin member 98, which is received in a slotted opening 100 in the yoke element 90. Other engagement methods which transfer the rotation of the yoke member to the lead screw are also contemplated, such as a fitting comprising a hexagonal pin 102 on the driven end 92, which is received in a corresponding hexagonal socket 104 in the universal joint 90, as shown in FIG. 5. Alternatively, the yoke 90 and lead screw 94 may be formed as a single component.

The lead screw 94 is exteriorly threaded along at least a portion of its length. The threads 110 engage corresponding threads 112 on an interior surface of a piston drive member 116 generally in the form of a cone. The pitch on the threads 110, 112 is such that as the lead screw rotates, the cone 116 moves towards the barrel chamber, carrying the piston 24 with it. In particular, as the lead screw 94 is rotated in a driving direction, the cone 116 converts the rotational movement of the lead screw into a linear advancement of the cone 116 in a fluid expelling direction.

Figure 6:
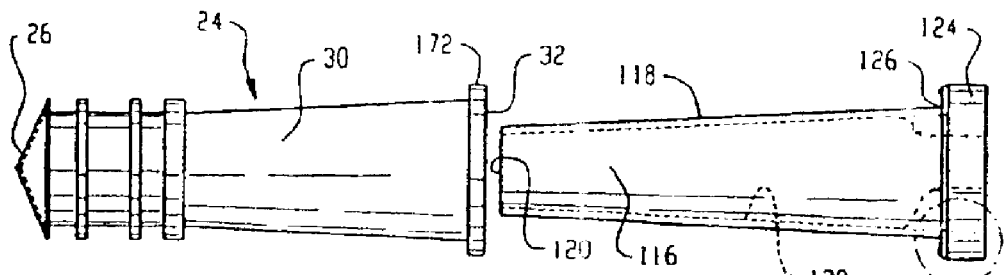
FIG. 6 is a side view of the piston and piston drive member of FIG. 1, showing the drive member fully separated from the piston.
Figure 7:
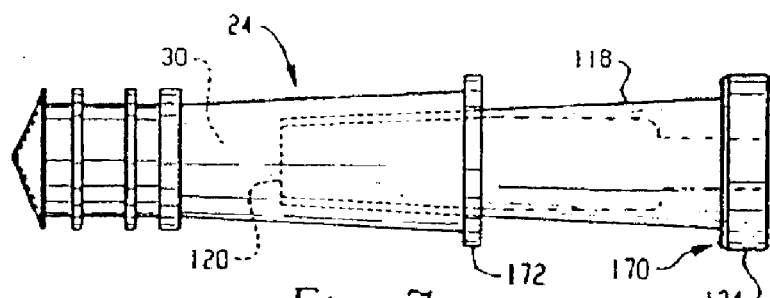
FIG. 7 is a side view of the piston and drive member of FIG. 6, showing the drive member partially separated from the piston.
Figure 8:
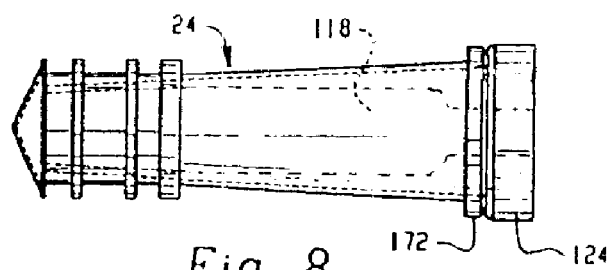
FIG. 8 is a side view of the piston and drive member of FIG. 6, showing the drive member abutting the piston.

As best shown in FIGS. 6–8, the cone 116 includes a longitudinally extending conical body 118, which is generally frustoconical in shape and which is received within the internal piston chamber 30. The body 118 is narrowest at an end 120, closest to the head portion 26 of the syringe 14. A flange 124 extends outwardly from an opposite end 126 of the conical body 118. The end 126 of the conical body 118 fits snugly in the open end 32 of the piston chamber 30, such that lateral movement of the piston 24 relative to the cone 116 is substantially or entirely eliminated. The conical body defines a longitudinal interior bore or passageway 128 which is threaded along at least a portion of its length, for receiving the lead screw 94 therethrough. It will be readily appreciated that the exact shape of the cone 116 is not limited to a conical shape as illustrated in FIGS. 1 and 6–8, but may be of any convenient shape to fit within the interior chamber 30 of the piston 24 and to provide guidance to the lead screw 94 so that the piston 24 moves longitudinally without excessive lateral wobbling. This ensures accurate and smooth dispensing of the medicament from the barrel chamber 18.

As shown in FIG. 1, the lead screw 94 may engage threads on the cone 116 at two, or more, spaced positions, one position 130, on the flange 124, adjacent the open end of the cone 116, the other 131, being adjacent the head end 26 of the piston 24, or the conical portion may be interiorly threaded along its entire length. Or, the distal end 96 of the lead screw may pass through a narrowed circular opening 132 in the cone tip 120 and be received in the end of the piston chamber adjacent the barrel chamber 18.

As best shown in FIG. 6–8, the cone 116 is a separate element from the piston 24 and slides into and out of the piston without any form of engagement therewith (other than touching contact). The tip 120 slidably contacts the cylindrical wall of the piston 24, or is slightly spaced therefrom. The cone 116 is thus configured for one-way guiding of the piston 24, i.e., the cone pushes the piston in a fluid expelling direction only. Retraction of the cone 116 (e.g., by rotation of the drive shaft 94 in an opposite direction to the driving direction) does not withdraw the piston 24 from the barrel 16.

In another embodiment, shown in FIG. 1, the narrow tip 120 of the cone 116 is externally threaded at 134 to engage corresponding threads 136 on the internal piston chamber 30. In this embodiment, the cone is configured for two-way driving of the piston 24. Retraction of the cone (e.g., by rotation of the drive shaft 94 in an opposite direction to the driving direction) withdraws the piston 24 from the barrel 16.

As best seen in FIGS. 9–10, the flange 124 includes a first portion 138, which is wider than the piston open end and a second portion 139, which is square shaped or otherwise defines an engagement surface. The first portion 138 provides a stop or abutting surface for abutting the piston 24. The second portion 139 of the flange 124 is guided by a longitudinally extending guide element 140, which extends generally parallel to the piston 24 and direction of travel of the cone 116. The guide element 140 contacts at least one of several flat peripheral surfaces 144 (four in the embodiment of FIG. 9) of the flange 124 and inhibits rotation of the flange and attached conical body 118. In the embodiment of FIGS. 9 and 10, the guide element 140 defines an interior bore 145 having a square cross section which snugly receives the corresponding square cross sectioned second portion 139. As the cone 116 is advanced, the piston 24 is driven into the barrel 16 of the syringe 14 and the medicament is expelled. Seals 146, such as o-rings, seal the gap between the piston 24 and the barrel 16.

Figure 11:
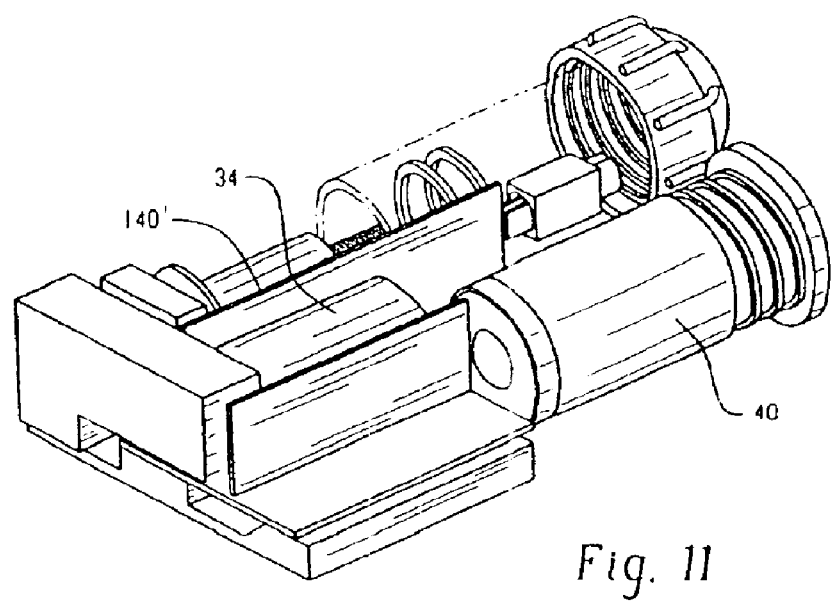
FIG. 11 is a perspective view of the infusion pump system FIG. 1.
Figure 12:
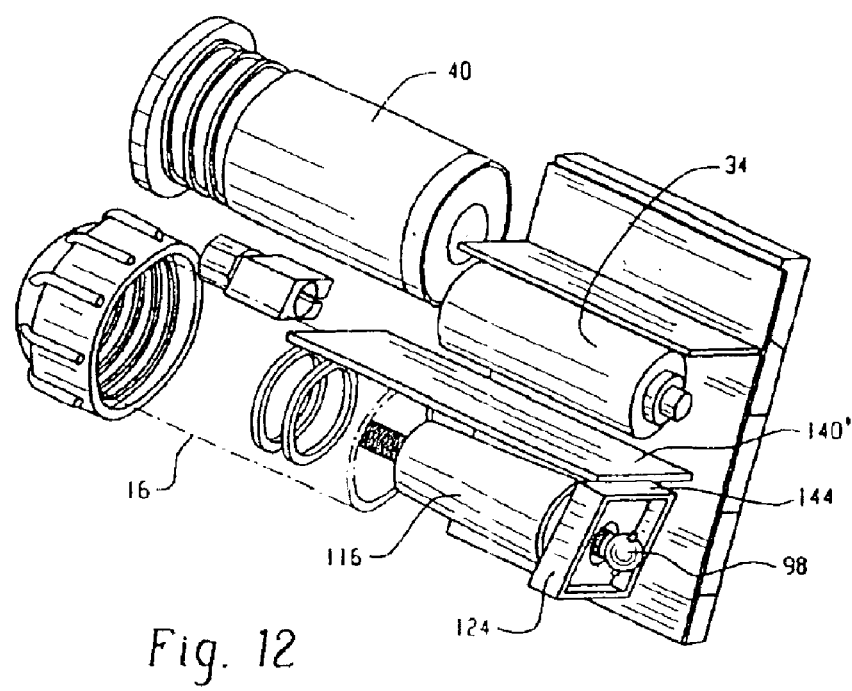
FIG. 12 is a top perspective view of the infusion pump system of of FIG. 1.

In an alternative embodiment, shown in FIG. 6, the entire flange 124 has a uniform, square cross section. In yet another embodiment, shown in FIGS. 11 and 12, the guide element 140' is in the form of a plate which extends parallel to the direction of travel of the cone 116. The guide element 140, 140' is mounted to the housing 10 or to another rigid support within the housing.

The travel of the cone 116 or piston 24 is preferably sensed by sensors 150, 152, which will be referred to herein as position sensors. For example, a first position sensor 150 detects when the cone 116 or piston 24 is in the "home" position (adjacent the driven end of the lead screw), as shown in FIG. 1. The sensor 150 may be an optical sensor, such as infra-red sensor, mounted adjacent the home position of the flange 124 (or other suitable portion of the cone 116 or piston 24). The sensor 150 includes a transmitter (not shown), such as an infra-red transmitter, and a receiver (not shown) such as an infra-red receiver. When the flange 124 is adjacent the sensor 150, for example, within about one millimeter of the sensor, the infra-red radiation from the transmitter strikes a reflective portion 156 of the flange 124, such as a piece of reflective metal, and is returned to the receiver. The sensor 150 detects when the signal is received and transmits a signal to the microprocessor controller to indicate that the cone 116 is in the "home" position. In an alternative embodiment, the head 26 or other part of the piston 24 includes the reflective portion.

A second position sensor 152, analogous to the first sensor 150, is positioned close to, or adjacent to the "end" or "barrel empty" position 157. The "end" position is the position that the reflective portion 156 is in when the piston head engages a dispensing end 158 of the barrel, i.e., where the flange 124 ends up when the piston 24 is depressed to the full extent of its travel. Preferably, the sensor 152's position is just before the end position 157 (i.e., slightly to the right of the end position, in the arrangement of FIG. 1). The second sensor 152 signals the microprocessor-controller 38 when the reflective portion 156 is adjacent to the sensor 152, and the microprocessor portion of the microprocessor-controller thereby recognizes that the cone 116 and piston 24 are approaching the end position. The controller portion of the microprocessor-controller instructs the motor 34 to cease advancing the shaft 42 and the piston 24 comes to a stop. In this way, the advancement of the piston 24 can be arrested before it hits a dispensing end 158 of the barrel 16, thereby avoiding potential damage to the drive system 36 or to the motor. This allows a "software" stop for the piston 24, rather than a "hard" stop. Alternatively, or additionally, the microprocessor may determine the position of the piston 24 from the signals received from the encoder 50 and by a calculation therefrom of the number of revolutions of the shaft 42. The microprocessor may use this determination as a check on the signals received from the second sensor 152, or to override the signal received from the second sensor when the two sets of signals are in conflict over the position of the piston 24. The microprocessor-controller 38 may signal an alarm, such as an audible alarm 160, a vibration alarm 162, and/or send a message to an LCD or other visual display 164 (see FIG. 1) to indicate to the user or care provider that the syringe 14 is empty and needs to be refilled or replaced. The housing 10 may also include a window 168 for providing a visual indication to the user of the quantity of medicament still present.

Figure 6A:
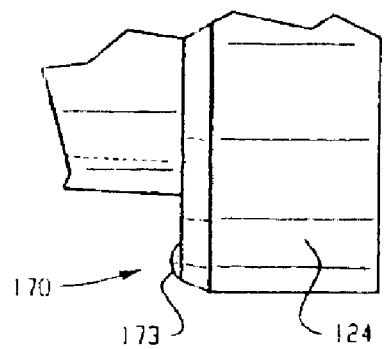
FIG. 6A is an enlarged side view of the piston drive member of FIG. 6, showing the position of a contact sensor.

With reference once more to FIGS. 6–8, a third sensor or proximity sensor 170 detects when the cone 116 is properly seated in the piston 24. During dispensing, the cone 116 is properly seated when it is in an abutting position, shown in FIG. 8, in which the cone flange 124 touches, or is closely adjacent to, a corresponding radially extending flange or lip 172 at the end of the piston body 118. In the event that a sudden change in ambient pressure, such as when the user travels by airplane, occurs, the piston 24 may separate from the cone 116, and move towards the spaced position shown in FIG. 7. The sensor 170 is electrically connected with the microprocessor-controller 38. The sensor 170 detects when such a separation occurs and a signal (or lack of signal) is sent to the microprocessor-controller 38. The microprocessor-controller 38 activates the audible alarm 160, the vibration alarm 162, and/or sends an appropriate message to the LCD or other visual display 164. The user is advised to open the housing 10 and ensure correct positioning of the piston 24. In one embodiment, illustrated in FIGS. 6–8, the sensor 170 includes a contact switch 173 (shown in greater detail in FIG. 6A), which is mounted to a surface of the cone flange 124 facing the piston flange 172. The contact switch 173 detects a pressure exerted by the piston flange 172 on the switch when the two flanges 172, 124 are closely adjacent or touching (FIG. 8). If the two flanges 172, 124 move apart, the switch 173 signals the resulting lack of pressure or reduced pressure to the microprocessor-controller 38. Alternatively, the sensor 170 sends a signal when the two flanges are abutting and a lack of signal is indicative of lack of abutment. It will also be appreciated that the contact switch 173 may alternatively be located on the piston flange 172.

Figure 13:
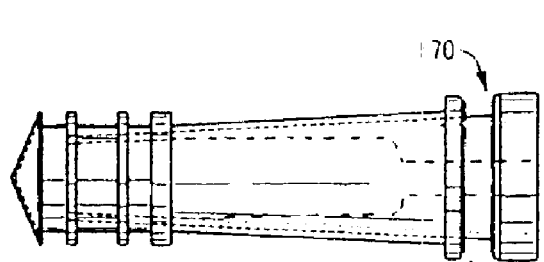
FIG. 13 a side view of an alternative embodiment of a contact sensor, piston, and drive member, according to the present invention.
Figure 13A:
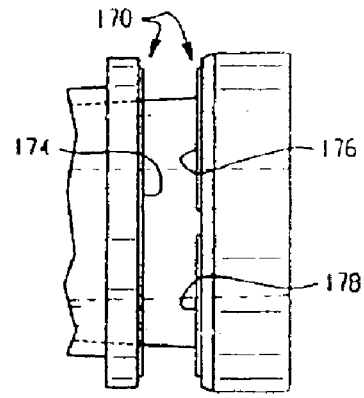
FIG. 13A is an enlarged side view of the drive member of FIG. 13, showing the position of the contact sensor parts.
Figure 14:
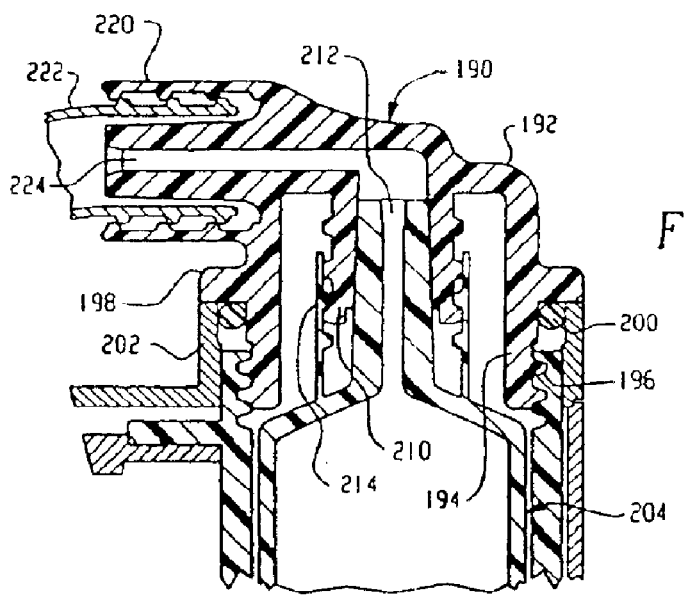
FIG. 14 is an enlarged sectional view of the cap of FIG. 1.
Figure 15:
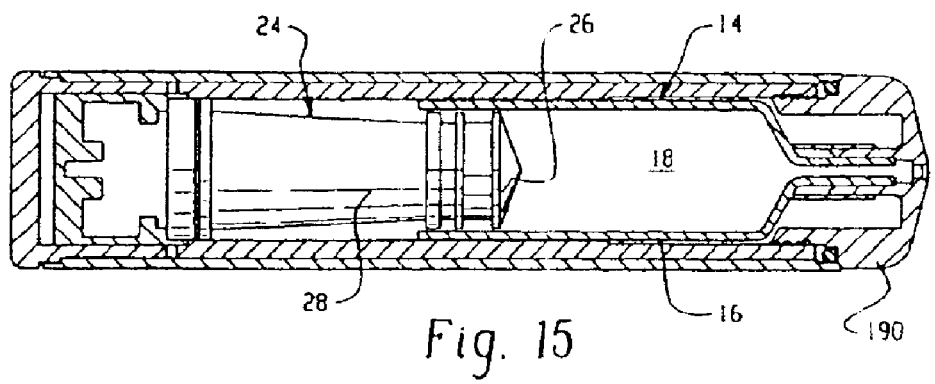
FIG. 15 is a side sectional view of the infusion pump system of FIG. 1.
Figure 16:
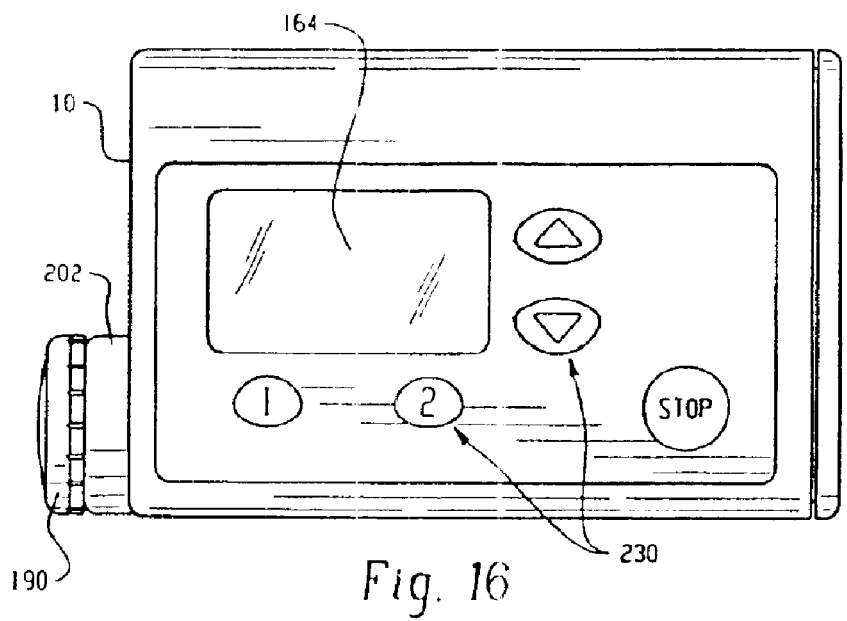
FIG. 16 is a front view of the infusion pump system of FIG. 1.
Figure 17:
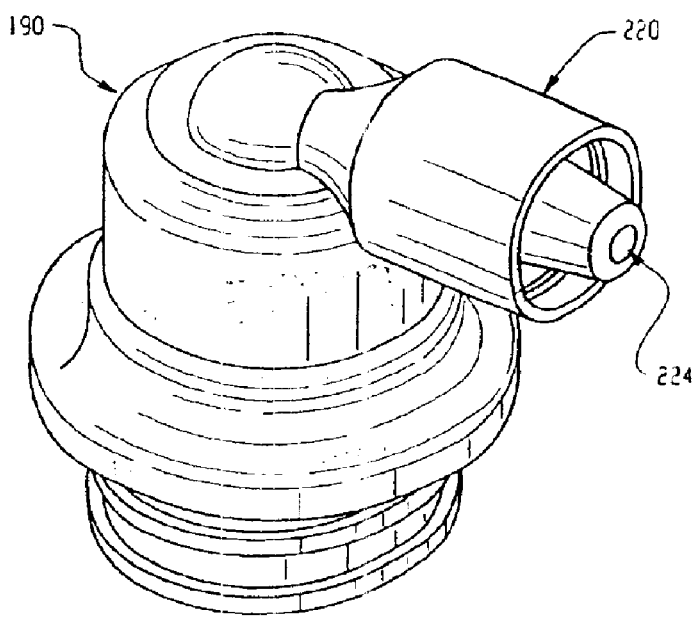
FIG. 17 is a perspective view of the cap of FIG. 1.

In another embodiment, shown in FIGS. 13 and 13A the sensor 170 includes a first conductive portion, such as a conductive ring 174, mounted to the piston flange 172, and a second conductive portion, such as two conductive half rings 176, 178 mounted to the cone flange 124, in facing relationship to the conductive ring 174. The two conductive half rings 176, 178 are electrically isolated from each other. The conductive ring 174 and a disk enscribed by the half rings 176, 178 have generally the same internal and external diameters such that when the flanges 172, 124 are positioned in abutting relationship, as in FIG. 8, an electrical circuit is formed. Specifically, electrical current supplied to one of the conductive half rings 176 flows to the conductive ring 174 and thence to the other of the conductive half rings 178. When the circuit is broken, as in when the piston 24 separates from the cone 116, a signal (or lack of signal) is sent to the microprocessor-controller 38. It will be appreciated that the positions of the ring 174 and half rings 176, 178 may alternatively be switched.

While the third sensor 170 has been described as sensing contact, or lack thereof, between the flanges 172, 124, it is to be appreciated that the sensor 170 may alternatively detect contact or lack of contact between other abutting surfaces of the cone 116 and the piston 24. For example, the sensor could sense an abutting relationship between the tip 120 of the cone and the head portion 26 of the piston 24. Electrical connections (not shown) connect the sensor 170 or one or more conductive portions thereof, with the microprocessor controller 38. Or, the sensor may be an optical sensor which detects when the piston 24 and cone 116 are within a prescribed distance range of one another.

With reference once more to FIG. 1, and reference also to FIGS. 14–17, an external cap 190 optionally secures the syringe 14 to the housing 10 and inhibits rotation of the syringe relative to the housing. In a preferred embodiment, best shown in FIG. 14, the cap includes a top 192. A first annular skirt 194 extends from a periphery of the top and is exteriorly threaded to engage corresponding interior threads on an annular engagement portion 196, which extends from the housing 10. The annular skirt includes a radial shelf 198. An O-ring 200 or other sealing member encircling the skirt. The radial shelf 198 holds the O-ring 200 in sealing engagement with a portion 202 of the housing 10, which is radially outward of the engagement portion. The O-ring inhibits the migration of water into the housing 10. The housing portions 196 and 202 are concentric and are joined together to define a circular opening 204 which is wide enough to receive the syringe 14 therethrough.

The cap 190 defines a second annular skirt 210, which depends from the top 192 and is spaced radially inward of the first skirt 194. The outlet 20 of the syringe 14 fits snugly within a first interior passage 212 defined by the second annular skirt 210. The second skirt 210 is exteriorly threaded and threadably engages a corresponding annular threaded portion 214 of the syringe 14. Specifically, the threaded portion 214 is a luer fitting, which extends from the syringe 14 in parallel with the outlet 20 and is radially spaced therefrom.

A second luer fitting 220 selectively connects the top 192 of the cap with an infusion line 222. The second luer fitting defines a second interior passage 224 which extends at right angles from the first interior passage 212.

After a syringe 14 is filled with a medical solution, such as insulin, the syringe is screwed on to the first luer fitting 212 of the syringe cap 190. Alternatively, the user may use prefilled, single use ampules. The piston 24 is depressed to purge air bubbles from the cap and infusion line. The syringe 14 is inserted into the housing 10 through the opening 204 and the cap 190, with the infusion line 222 attached, is rotated clockwise to lock the cap to the housing.

The piston 24 slides over the conical sides of the cone 116 (which is already retracted to its home position), and is thereby guided into its correct position in the housing. When the piston 24 is fully inserted, i.e., with the lip 172 of the piston 24 engaging or adjacent to the cone flange 124, the user programs the microprocessor-controller by way of a user-microprocessor interface 230, such as a keypad, touch screen, or other suitable interface (see FIG. 16). The user may select, for example, from a range of preprogrammed injection schemes or enter information, such as blood glucose levels, expected or actual carbohydrate intake, etc. in order for the microprocessor to calculate an appropriate infusion regimen. Or, the user may enter the amount of insulin to be infused in a selected time period. The infusion line 222 may be connected with an infusion set (not shown) or other suitable infusion device for supplying the medication to the user's body.

In the embodiment of FIG. 1 where the cone 116 is exteriorly threaded, the piston 24 is rotated a few turns (e.g., by grasping the syringe 14 adjacent the connector portion 20 and turning it) to engage the internal piston threads 136 with the corresponding threads 134 of the cone, thereby locking the piston 24 to the cone 116.

The motor 34 rotates the drive shaft and the lead screw rotates, as described above. The interior threads on the cone 116 cause the lead screw and cone to begin to separate, pushing the cone and piston 24 in the dispensing direction.

Prior to making a connection between the infusion line 222 and an infusion set (not shown), the user preferably instructs the pump microprocessor-controller 38 to conduct a purge phase to clear the infusion line 222 of air by passing a quantity of the medicament through the line. The user visually observes when the line is filled with the medicament and instructs the microprocessor 38 to halt the purge phase. The microprocessor detects that the cone flange 124 is no longer against the first sensor 150 and also determines the quantity of medicament expelled during the purge phase from the signals from the two-phase encoder 50.

The microprocessor-controller 38 then controls the operation of the pump through the selected cycle. Using the information from the two-phase encoder 50, the microprocessor keeps a check of the amount of medicament dispensed and provides a visual display to the user on the LCD display 164. This may be a numerical display of the amount of insulin and/or in the form of a bar which decreases in size or in number of elements (similar to the indicator of battery level on a cellular phone) or other visual indication of decreasing medicament supplies. The controller uses this value as a second check as to when the medicament supply is about to run out. When the second sensor detects that the cone flange 124 is in the "empty" position, it signals the microprocessor-controller, which in turn stops the advancement of the motor. By way of the LCD display 164, the microprocessor-controller instructs the user to remove the syringe 14. Once the user has removed the syringe 14, the user signals the microprocessor that the syringe has been removed by making a suitable entry on the interface 230. The controller then reverses the direction of advancement of the motor 34 and the motor backs the cone 116 up to the "home" position. When the cone "home" position is detected by the sensor 150, the microprocessor instructs the user, by way of the LCD display 164, to insert a fresh syringe and the process is repeated.

In the event that an occlusion blocks the line 222 and reduces the flow of medicament to the user, an occlusion sensor system 240 detects the occlusion and signals an alarm to indicate to the user that the medicament is not being administered at the appropriate rate. As shown in FIG. 1, the occlusion sensor 240 is integral with the microprocessor-controller 38, although a separate occlusion sensor is also contemplated. The alarm can be the visual alarm, such as on the LCD display 164, the audible alarm 160, or the vibration alarm 162. In the device of FIG. 1, each of these alarms is employed. The vibration alarm 162 preferably takes the form of a vibrating motor, which is connected with the microprocessor. The user may select which of the alarm functions is to be in operation, for example, by switching off the audible alarm 160 and activating the vibration alarm 162.

In one preferred embodiment, the occlusion sensor system 240 operates by detecting stalling of the motor 34. If an occlusion in the line occurs, the pressure build up in the line inhibits advancement of the piston, which, in turn, reduces or prevents rotation of the lead screw, gears and motor shaft, and causes the motor to stop or reduce its advancement. For example, the microprocessor-controller 38 detects if the signals from the two-phase encoder 50 indicate that the motor is not advancing or is advancing too slowly. For example, in this embodiment of the occlusion sensor, the microprocessor-controller counts how many signals are received from the encoder in a preselected time period and determines whether the number of signals is less than expected. Or, the microprocessor-controller detects an absence of any encoder signals in a preselected time period.

In an alternative embodiment of an occlusion sensor 240, shown in FIG. 4, a pressure transducer 250 or micro switch may be attached to a shaft portion 252 of the universal joint 90 to detect build-up of pressure in the lead screw 94 caused by the piston 24 being unable to traverse. The transducer signals the microprocessor-controller 38, which, if the pressure is above a preselected minimum pressure, signals the alarm, as with the other embodiment.

As can be seen, the arrangement of the motor 34 and drive shaft 42 in parallel with and adjacent to the syringe 14 and lead screw 94 makes good use of the space within the housing 10 and minimizes the overall length of the housing. Additionally, since neither the lead screw nor the drive shaft advances longitudinally in the housing 10 (both simply rotate), the housing 10 does not have to be enlarged to accommodate for longitudinal movement of these components. For example, a convenient size for the housing 10 is about 75 mm in length and about 45 mm in width.

Figure 20:
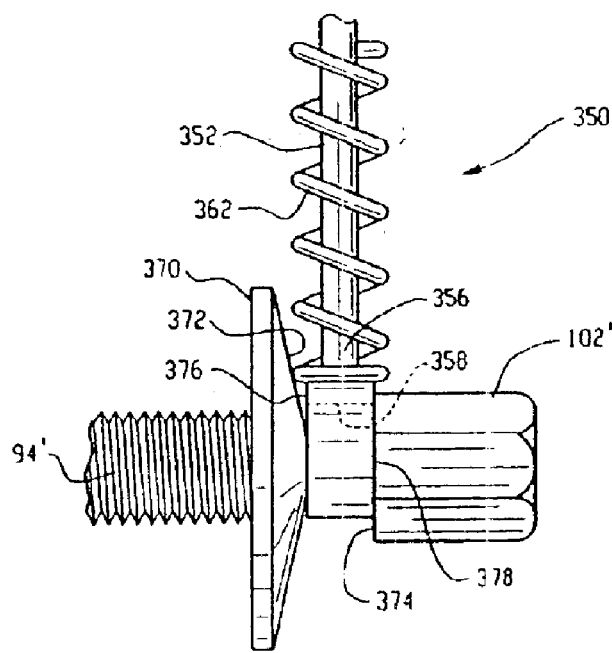
FIG. 20 is an enlarged view of the clamping member of FIG. 18.
Figure 21:
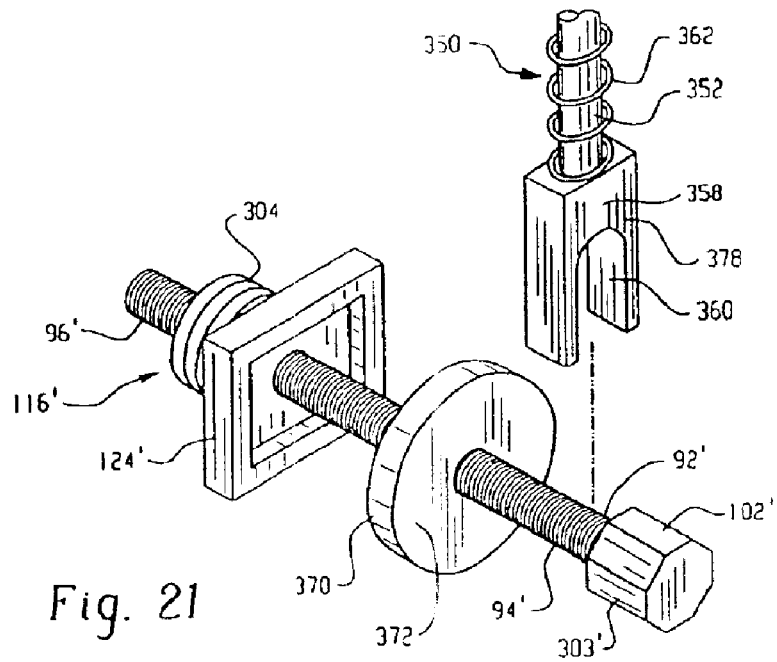
FIG. 21 is an enlarged perspective view of the clamping member and lead screw of FIG. 18.

FIGS. 18 to 23 show an alternative embodiment of a portable pump system where analogous components will be indicated by a prime (') and new components are given new numbers. The system includes a housing 10', motor (not shown), drive shaft (not shown), and gear box analogous to the housing 10, drive shaft 42, and gear box 54 of FIG. 1. In this embodiment, however, a lead screw 94' has a fitting 102', such as a pin, at a rearward end or driven end 92' thereof, which is configured for receipt by a correspondingly-shaped cavity 302 in the final gear 60' of the gear box. In this embodiment, the universal joint is omitted, although it is also contemplated that a universal joint 98 similar to that shown in FIG. 4 may alternatively be used to couple the lead screw to the gear box. As shown in FIG. 21, the fitting 102' preferably has an angled cross section, such as a hexagonal cross section as shown, or square cross section, so that the rotational movements of the gear 60' are transferred to the lead screw 94'. Exterior surfaces 303 of the fitting engage corresponding abutting surfaces 303' of the cavity 302. It should also be appreciated that the shapes of the fitting 102' and gear may be reversed, i.e., with the fitting defining a hexagonal or similar cavity shaped to receive a corresponding pin or protrusion on the gear.

Alternatively, the lead screw 94' may be threadably or otherwise releasably connected with the gear 60' of the gear box.

Figure 19:
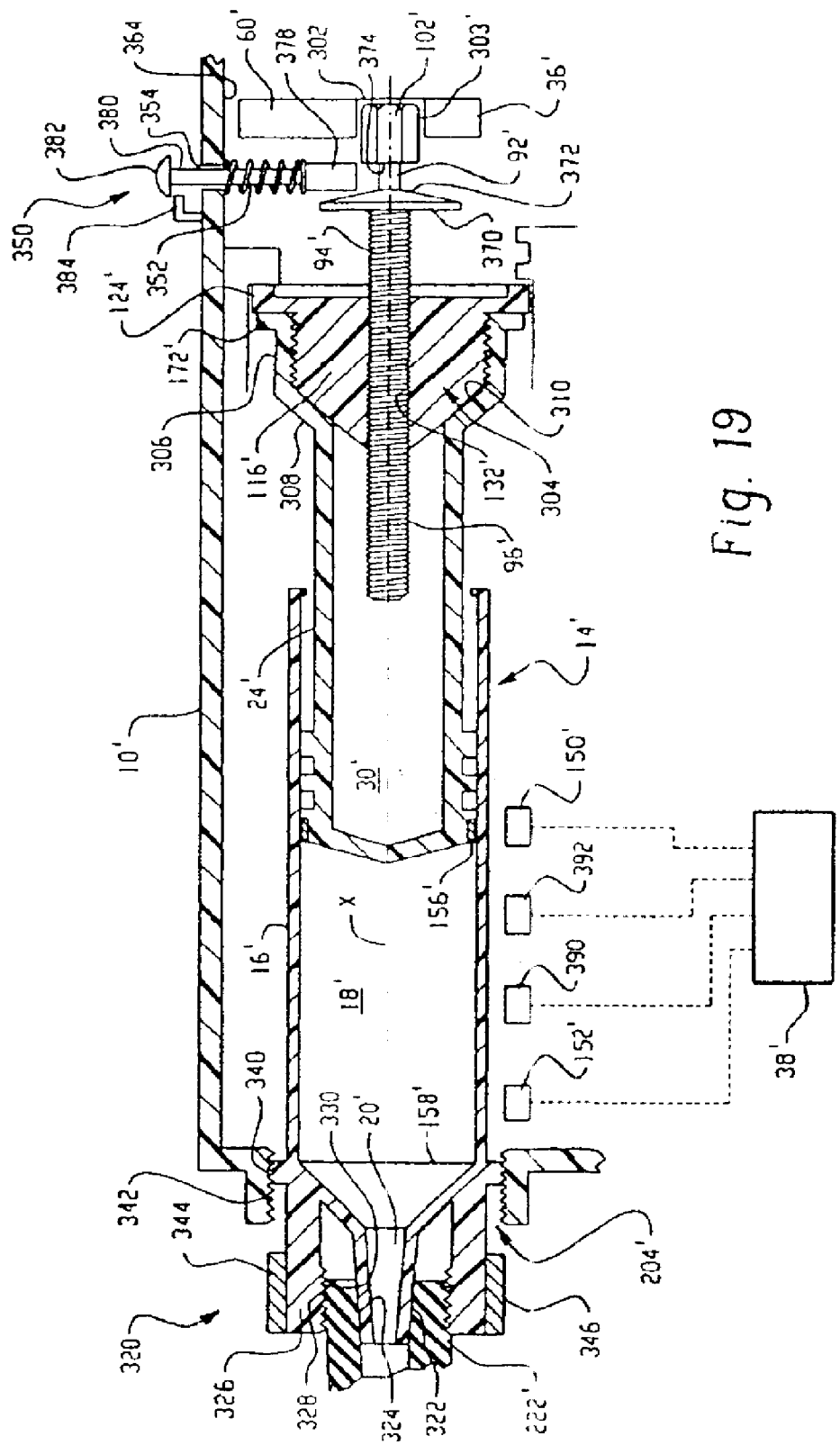
FIG. 19 is a side sectional view of the infusion pump of FIG. 18.

As with prior embodiments, rotation of the lead screw 94' is converted to linear motion of a piston drive member 116'. In this embodiment, the piston drive member 116' is threadably connected to the piston 24'. Specifically, the drive nut 116' includes a threaded portion 304, which is externally threaded and is configured for threadable connection to an internally threaded rearward end 306 of the piston. As is shown in FIG. 19, the rearward end 306 of the piston 24' is preferably widened, relative to the head 26' of the piston, and defines a flange 172' which abuts a corresponding flange 124' on the drive nut 116' when the two parts are coupled together. As shown in FIG. 19, the widened end has a tapered portion 308, which abuts a corresponding tapered portion 310 of the drive nut 116'. In this embodiment, the piston drive member 116' extends only a short distance into the piston 24' and the abutment of the tapered portions 308, 310 and flanges 172', 124' and engagement of the threads assist in maintaining the axial alignment of the drive nut 116' and piston 24' during advancement of the piston. As will be appreciated, the drive nut 116' of this embodiment is configured for two-way guidance of the piston, i.e., the drive nut optionally drives the piston 24' linearly, both in the advancement (dispensing) stage and in a subsequent piston withdrawal stage, although it is also contemplated that the piston is not withdrawn by the drive nut, as will be described in greater detail below.

As with the embodiments of FIGS. 9–12 a guiding member (not shown) analogous to guiding member 140 preferably guides the flange 124' of the drive nut 116' to ensure that the drive nut and piston 24' advance linearly towards the syringe barrel 16' as the lead screw 94' rotates.

The drive nut 116' defines an opening or axial bore 132', which is internally threaded to receive a forward or distal end 96' of the threaded lead screw 94' therethrough. In this embodiment, the bore 132' is threaded along its entire length and the lead screw 94' extends into the interior chamber 30' of the piston 24', at least during the initial period of dispensing.

Figure 18:
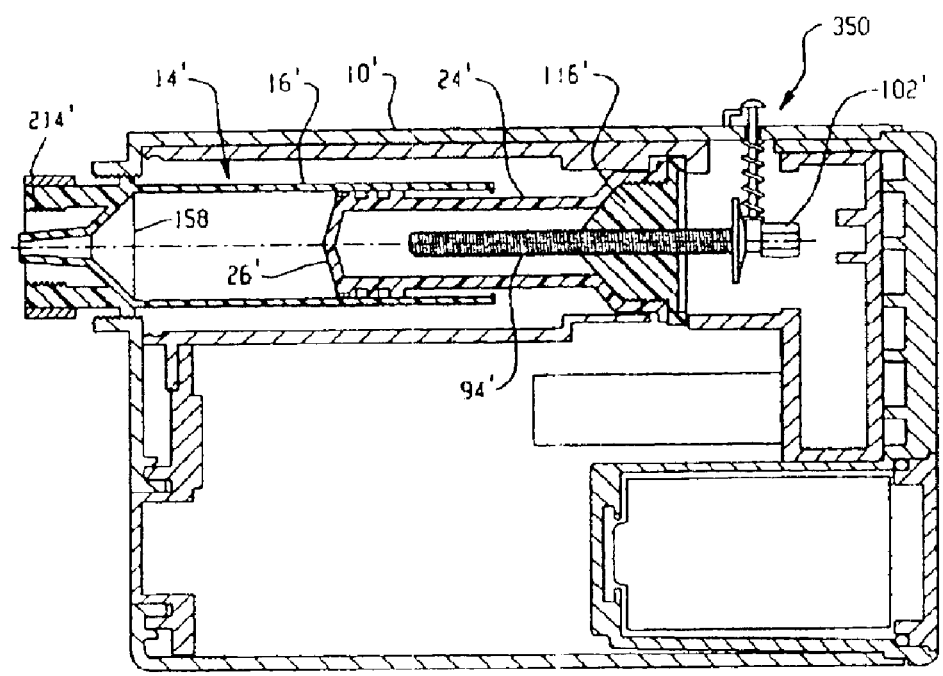
FIG. 18 is a top plan view of another embodiment of an infusion pump according to the present invention.

In this embodiment, the cap 190 of FIGS. 1–17 is optionally replaced by a mounting member 320, which is integral with the syringe barrel 16'. The mounting member serves the same functions as the cap 190, i.e., releasably mounting the syringe 14' to the housing 10' and providing a means for attachment of an infusion line 222'. In this embodiment, the syringe has a luer connection 214' adjacent the dispensing outlet 24' analogous to that shown in FIG. 14, but in this embodiment, the luer connection 214' attaches directly to the infusion line 222', rather than to a portion of a cap. Specifically, as shown in FIGS. 18 and 19, the outlet 20' has a tapered exterior surface 322, which slidingly engages a corresponding tapered surface 324 of the infusion line or a fitting thereon. An annular cylindrical portion 326 extends forward from the syringe barrel 16', and is spaced radially outward of the outlet 20'. The cylindrical portion 326 is interiorly threaded at 328 to engage corresponding exterior threads 330 on the infusion line or fitting connected therewith.

Figure 22:
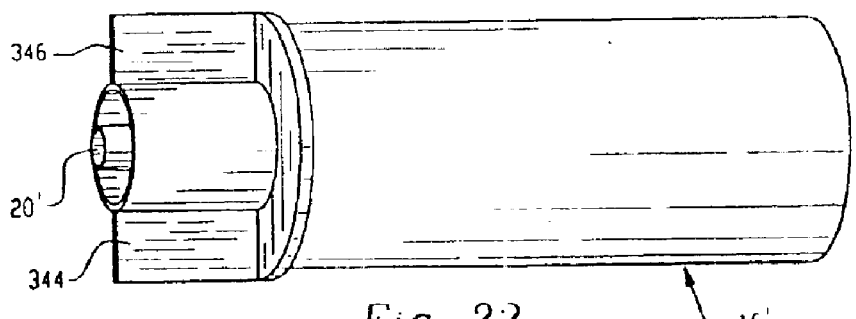
FIG. 22 is an enlarged perspective view of the syringe barrel of FIG. 18.

Exterior threads 340 on the forward end 158' of the syringe barrel 16' are configured for threadable connection with corresponding interior threads 342 around the housing opening 204'. As best shown in FIG. 22, a pair of gripping flanges 344, 346 extend radially outward of the cylindrical portion for ease of gripping by a user. To attach the syringe 14' to the housing 10', the user inserts the syringe through the housing opening 204' into the housing and grips the griping flanges in one hand while holding the housing in the other. The user then rotates the syringe to threadably attach the threads 340, 342 and thus lock the syringe to the housing.

Figure 23:
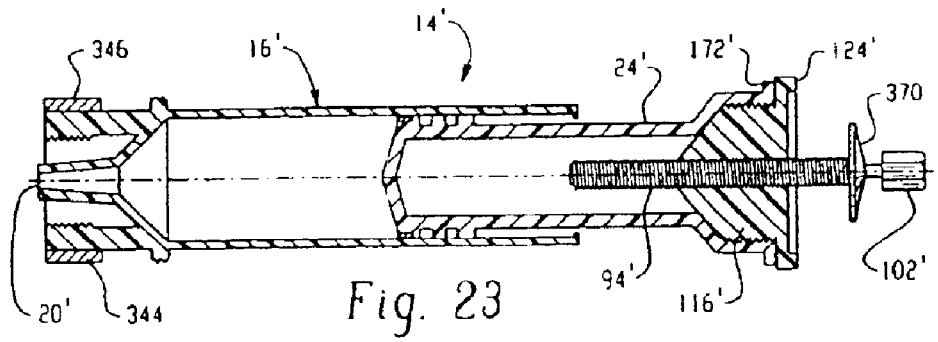
FIG. 23 is a side sectional view of the syringe barrel, piston, drive nut, and lead screw of FIG. 18.

As shown in FIG. 23, the drive nut 116' and lead screw 94' are preferably connected with the prefilled syringe 14' outside the housing, i.e., prior to inserting the syringe into the housing. Specifically, the drive nut 116', with the lead screw 94' already attached, is first threadably connected to the syringe by rotating the syringe or drive nut to threadably couple the two components. Prior to or after coupling the drive nut 116' to the piston 24', the lead screw 94' is correctly axially positioned relative to the drive nut and piston, such that when the syringe is positioned into in the housing, the fitting 102' is received in the cavity 302 and the threads 340 of the syringe are positioned for engagement of the threads 342. Preferably, the positioning of the lead screw 94' is carried out by the controller 38', after the medicament has been dispensed. The controller instructs the drive system (not shown) to rotate the lead screw so that it moves forward, relative to the drive nut, 116' to its home position, ready to begin dispensing again.

With particular reference to FIGS. 19–21, a clamping member or clip 350 serves to selectively lock the rearward portion 92' of the lead screw so that the lead screw fitting 102' remains engaged with the gear 60' during advancement of the piston 24'. The clamping member 350 is carried by the housing 10' and includes a post 352, which is received through an opening 354 in the housing. An interior end 356 of the post defines a slotted portion 358, which defines a slot 360 (FIG. 21) configured for receiving the rearward portion 92' of the leadscrew therein. The post is biased to an engaged position (FIGS. 18 and 20) by a spring 362, which is held under compression between the slotted portion 358 and an adjacent interior surface 364 of the housing 10'.

A projection, such as a gasket 370, is preferably formed from rubber or other suitable resiliently compressible material. The gasket is mounted to the leadscrew 94' in a fixed position, adjacent the rearward portion 92'. The gasket is spaced from the fitting 102' by a distance just sufficient to receive the slotted portion 358 therebetween such that when the clamping member 350 is in the engaged position, the lead screw 94' is prevented or inhibited from moving, in either direction along axis x, relative to the gear 60' and housing. Most preferably, the gasket 370 and fitting 102' act as projections whose facing surfaces 372, 374 abut corresponding opposing sides surfaces 376, 378 of the slotted portion 358. Since the gasket 370 is formed from a resiliently compressible material, such as rubber, the slotted portion is gripped between the gasket and the fitting. The lead screw is still able to rotate, however, when the clamping member is in the engaged position, and thereby advance the piston drive member and piston. As shown in FIG. 20, the surface 372 is preferably tapered to provide a camming surface which assists in guiding the slotted portion 358 during movement between the disengaged and engaged positions.

The clamping member 350, in cooperation with the fitting 102', prevents linear movement of the lead screw 94' in a dispensing direction, thereby preventing unintended dispensing of the medicament from the syringe. For example, in the event of a sudden drop in ambient pressure, the suction forces created tend to try to draw the piston 24' into the syringe barrel 16' and dispense additional medicament. The clamping member 350 holds the shaft 94' in a fixed linear position, relative to the syringe barrel and housing and since the shaft 94', drive nut 116' and piston are all coupled together, the piston is inhibited from advancing. Additionally, the gasket 370 in cooperation with the clamping member prevents the leadscrew 94' from moving in a piston retracting direction (i.e., opposite to the advancing direction) in the event that a sudden increase in ambient pressure or other reason tends to move the syringe piston 24' in a retracting direction. In this way, the amount of each bolus of medicament dispensed is correctly metered by the controller 38'.

An upper end 380 of the post 352, which is positioned outside of the housing 10', defines a flange 382 or other engagement member. The clamping member 350 is held in a disengaged position (FIG. 19) by a stop 384, such as a movable or releasable member. The stop 384 engages the engagement member 382 during the period of insertion of the syringe 14' into the housing 10'. When the syringe 14' is correctly positioned in and attached to the housing, the stop 384 is rotated, depressed, or otherwise actuated by the user (or by the controller 38') to release the flange 382 and post 352. The post 352, under the biasing action of the spring 362, then moves from the disengaged position of FIG. 19 to the engaged position of FIG. 20.

As with prior embodiments, position sensors 150', 152' detect the linear position of the piston. In this embodiment, the reflective portion 156' is shown on the piston head, although it is also contemplated that the reflective portion 156' may be positioned elsewhere on the piston 24' or drive nut 116'. Optionally, additional position sensors 390, 392 are positioned at spaced distances apart between the two position sensors 150' and 152' for use in determining or providing a check on the incremental amounts of liquid dispensed. While two additional position sensors 390, 292 are shown in FIG. 19, it is to be appreciated that fewer or more additional position sensors may be employed.

As will readily be appreciated, the infusion pump and drive system of the present invention has applications outside the medical field and is not limited to use in an infusion system.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A liquid delivery system comprising:
    a housing which accommodates a syringe containing the liquid;
    a motor carried by the housing; and
    a drive system, operatively connected with the motor, which advances a piston of the syringe to expel liquid from a barrel of the syringe, the drive system including:
        a rotatable gear;
        a threaded rotatable shaft, the shaft including a fitting configured for permanent engagement with the rotatable gear;
        a piston drive member which linearly advances the piston, the drive member defining a threaded portion which engages threads of the shaft, the piston drive member advancing linearly as the shaft rotates; and
        a guide element adapted to telescopically receive the piston drive member and inhibit rotation of the piston drive member during linear advancement of the piston drive member.

2. The liquid delivery system of claim 1, wherein the drive member defines an engagement portion which selectively engages an engagement portion of the piston.

3. The liquid delivery system of claim 1, wherein the drive member engagement portion defines threads which threadably engage corresponding threads of the piston engagement portion.

4. The liquid delivery system of claim 1, wherein one of the fitting and the rotatable gear defines a cavity configured for sliding receipt of a pin on the other of the fitting and the gear, the pin and the cavity having surfaces which contact each other causing the fitting to rotate as the gear rotates.

5. The liquid delivery system of claim 1, wherein the piston drive member includes a portion which is received within the piston.

6. The liquid delivery system of claim 1, wherein the piston drive member includes a flange which abuts a flange of the piston during advancement of the piston.

7. The liquid delivery system of claim 1, further including:
    a proximity sensor which senses occurrence of at least one of two states:
        (a) the piston drive member abutting the piston, and
        (b) the piston drive member not abutting the piston;
    a microprocessor which receives a signal from the proximity sensor and alerts a user of the delivery system of the occurrence of at least one of state (a) and state (b).

8. The liquid delivery system of claim 7, wherein the microprocessor alerts the user by actuating an alarm when state (b) occurs.

9. The liquid delivery system of claim 7, wherein the proximity sensor includes at least one of:
    (a) a contact switch which is located on an abutting surface of one of the piston drive member and the piston; and
    (b) a first electrically conductive member on a surface one of the piston drive member and the piston and a second electrically conductive member on a surface of the other of the piston drive member and the piston, such that current flows between the first and second electrically conductive members when the surfaces are abutting.

10. The liquid delivery system of claim 1, wherein the motor is a stepper motor and further including:
    an encoder which detects step movements of the motor; and
    an occlusion sensor which detects when there is an occlusion in the delivery system, the occlusion sensor receiving signals from the encoder and determining an occlusion from a reduction in a speed of the step movements.

11. The liquid delivery system of claim 1, wherein the piston drive member further includes an extension member attachable to the guide element to provide a coupling relationship with the guide member during linear advancement of the piston, the guide member movable along the threaded rotatable shaft during linear advancement of the piston.

12. A liquid delivery system comprising:
    a housing which accommodates a syringe containing the liquid;
    a motor carried by the housing;
    a drive system, operatively connected with the motor, which advances a piston of the syringe to expel liquid from a barrel of the syringe, the drive system including:
        a threaded rotatable shaft; and
        a piston drive member, which linearly advances the piston, the drive member defining an interior threaded portion which engages exterior threads of the shaft, and an exterior threaded portion which engages interior threads of the piston drive member thereby advancing the piston linearly as the shaft rotates; and
    a clamping member which selectively clamps the shaft against linear advancement, relative to the housing, in at least a dispensing direction, while permitting the shaft to rotate relative thereto.

13. The liquid delivery system of claim 12, wherein the clamping member includes:
    a post which defines a slot for receiving the shaft therein; and
    a biasing member which biases the post to an engaged position, in which the slot receives the shaft.

14. The liquid delivery system of claim 13, wherein the biasing member includes a spring.

15. The liquid delivery system of claim 13, further including a stop which, when actuated, allows the post to move from a disengaged position, in which the slot is spaced from the shaft, to the engaged position, in which the slot receives the shaft.

16. A liquid delivery system comprising:
    a housing which accommodates a syringe containing the liquid;
    a motor carried by the housing; and
    a drive system, operatively connected with the motor, which advances a piston of the syringe to expel liquid from a barrel of the syringe, the drive system including:

a threaded rotatable shaft; and a piston drive member, which linearly advances the piston, the drive member defining an interior threaded portion which engages exterior threads of the shaft, and an exterior threaded portion which engages interior threads of the piston drive member thereby advancing the piston linearly as the shaft rotates, wherein the housing defines an opening for receiving the syringe therethrough, the opening defining threads for engaging threads on the syringe barrel to lock the syringe to the housing.

17. A liquid delivery system comprising:

a housing which accommodates a syringe containing the liquid;

a motor carried by the housing;

a drive system, operatively connected with the motor, which advances a piston of the syringe to expel liquid from a barrel of the syringe, the drive system including:

a threaded rotatable shaft; and a piston drive member, which linearly advances the piston, the drive member defining an interior threaded portion which engages exterior threads of the shaft, and an exterior threaded portion which engages interior threads of the piston drive member thereby advancing the piston linearly as the shaft rotates;

a proximity sensor which senses occurrence of at least one of two states:

(a) the piston drive member abutting the piston, and (b) the piston drive member not abutting the piston; and a microprocessor which receives a signal from the proximity sensor and alerts a user of the delivery system of the occurrence of at least one of state (a) and state (b);

wherein the piston drive member defines a first flange and the piston defines a second flange, at least a portion of the proximity sensor being associated with at least one of the first and second flanges.

18. A liquid delivery system comprising:

a housing which accommodates a syringe containing the liquid;

a motor carried by the housing;

a drive system, operatively connected with the motor, which advances a piston of the syringe to expel liquid from a barrel of the syringe, the drive system including:

a threaded rotatable shaft; and a piston drive member, which linearly advances the piston, the drive member defining an interior threaded portion which engages exterior threads of the shaft, and an exterior threaded portion which engages interior threads of the piston drive member thereby advancing the piston linearly as the shaft rotates;

a first position sensor which detects when at least one of the piston and the piston drive member is in a first position; and a second position sensor which detects when the at least one of the piston and the piston drive member is in a second position, linearly spaced from the first position.

19. The liquid delivery system of claim 18, wherein when the at least one of the piston and the piston drive member is in the first position, the piston is spaced from a liquid outlet of the syringe through which the liquid is dispensed and wherein when the at least one of the piston and the piston drive member is in the second position, the piston is closely adjacent the liquid outlet of the syringe.

20. A liquid delivery system comprising:

a housing which accommodates a syringe containing the liquid;

a motor carried by the housing;

a drive system, operatively connected with the motor, which advances a piston of the syringe to expel liquid from a barrel of the syringe, the drive system including:

a threaded rotatable shaft; and a piston drive member, which linearly advances the piston, the drive member defining an interior threaded portion which engages exterior threads of the shaft, and an exterior threaded portion which engages interior threads of the piston drive member thereby advancing the piston linearly as the shaft rotates;

a cap, which selectively connects the syringe to the housing, the cap including:

a first threaded portion which threadably engages a threaded portion on the syringe; and a second threaded portion which threadably engages a threaded portion on the housing.

21. An infusion system comprising:

a housing which receives a cartridge, the housing defining an opening for receiving the cartridge therethrough;

a threaded shaft which is selectively drivingly coupled with a piston of the cartridge, the threaded shaft linearly advancing the piston as the shaft rotates to expel a liquid from a barrel of the cartridge; and a clamping member which is selectively actuated to engage the shaft and thereby inhibit linear advancement of the shaft, relative to the barrel.

22. The infusion system of claim 21, wherein the clamping member includes a slotted portion which defines a slot configured to receive a portion of the shaft therein and the shaft includes first and second spaced projections which abut the slotted portion when the clamping member is in an engaged position in which the slot receives the shaft portion.

23. The system of claim 21, wherein the shaft is removable from the housing with the cartridge.

24. The infusion system of claim 21, wherein, the housing opening defines threads for releasably engaging corresponding threads on the cartridge.

* * * * *